(12) United States Patent
Chen

(10) Patent No.: US 6,759,435 B1
(45) Date of Patent: Jul. 6, 2004

(54) ANTIDEPRESSANT DRUGS AND METHODS

(75) Inventor: Larry Chen, Beijing (CN)

(73) Assignee: A.P. Group Inc., Nashua, NH (US)

( * ) Notice: Subject to any disclaimer, the term of this patent is extended or adjusted under 35 U.S.C. 154(b) by 0 days.

(21) Appl. No.: 10/612,489

(22) Filed: Jul. 3, 2003

(51) Int. Cl.⁷ ...................... A01N 33/02; A61K 31/135; C07C 211/00
(52) U.S. Cl. .................. 514/648; 564/316; 564/319
(58) Field of Search .................. 514/648; 564/316, 564/319

(56) References Cited

PUBLICATIONS

Database CAPLUS on STN, Acc. No. 1991:514088, Christenson et al., Tetrahedron (1991), 47(26), p. 4739–52 (abstract).*

* cited by examiner

Primary Examiner—Brian Davis

(57) ABSTRACT

Novel amines are potent and selective serotonin reuptake inhibitors and as such can be used in the treatment of depression and other mental disorders.

18 Claims, No Drawings

ANTIDEPRESSANT DRUGS AND METHODS

BACKGROUND OF THE INVENTION

1. Field of the Invention

The invention relates generally to treatment of disease states and conditions which can be improved by administering a serotonin reuptake inhibitor (e.g., depression), and more specifically to novel amine compounds and pharmaceutical compositions thereof which are useful in the treatment of said disease states.

2. Description of Related Art

Major depression represents one of the most common mental illnesses, affecting between 5–10% of the population. The disease is characterized by extreme changes in mood which may also be associated with psychoses. It has generally been found that most antidepressant agents exert significant effects on the regulation of monoamine neurotransmitters, including serotonin.

A number of types of antidepressants have been developed in recent years. Many of these compounds regulate serotonin (5-hydroxytryptamine; 5-HT). Trazodone controls the actions of 5-HT while fluoxetine is a potent and selective inhibitor of 5-HT reuptake. 3-Chloroimipramine which inhibits both 5-HT and norepinephrine reuptake has been extensively used as an antidepressant in Europe and Canada. Other compounds which are of current interest or have been examined as antidepressants include fluvoxamine, citalopram, zimeldine, sertraline, bupropion and nomifensine.

The serotonergic neural system of the brain have been shown to influence a variety of physiologic functions, and antidepressants have the ability to treat in mammals, including humans, a variety of disorders associated with this neural system, such as eating disorders, depression, obsessive compulsive disorders, panic disorders, alcoholism, pain, memory deficits and anxiety. Other indications for antidepressants include unipolar depression, dysthymia, bipolar depression, treatment-resistant depression, depression in the medically ill, panic disorder, obsessive-compulsive disorder, eating disorders, social phobia, and premenstrual dysphoric disorder.

The adverse effects occurring most frequently during treatment with selective serotonin reuptake inhibitors (SSRI(s)) are gastrointestinal disturbances, such as, for example nausea, diarrhoea/loose stools, constipation, with an incidence of 6 to 37% (Drugs 43 (Suppl. 2), 1992). Nausea is the main adverse effect in terms of incidence. These adverse effects, although mild to moderate in severity, shy some patients away from treatment with SSRIs. The percentage of patients withdrawing because of nausea ranges from 3 to 8% of the patients. Moreover it has been frequently observed that after administration of SSRIs, patients suffer from dyspepsia. Known antidepressants also cause a variety of other adverse effects including anorexia, dry mouth, headache, nervousness, skin rash, sleep problems, somnolence, liver toxicity, mania, increased urination, seizures, sweating increase, tremors, and Tourette's syndrome. Current research is beginning to unveil that many of these drugs produce undesirable physiological side effects (Sipgset, O. Drug Saf. 1999. 20(3):277–287; Pache, P. Curr. Med Chem. 1999. 6(6): 46–480).

Often, these drugs also take about six to eight weeks to exhibit any desirable therapeutic effects. This time period can be prolonged when the correct drug or combinations of drugs has to be determined, by trial and error, before any therapeutic effects are observed.

We have thus focused our efforts on the development of novel antidepressants, which do not suffer from the side effects associated with presently known serotonin reuptake inhibitors and which take shorter to exhibit desirable therapeutic effects.

BRIEF SUMMARY OF THE INVENTION

In certain embodiments, this invention is directed to novel amine compounds, which are potent, and selective serotonin reuptake inhibitors.

In certain embodiments, this invention is directed to compounds of the formula (I) and pharmaceutically acceptable tautomers and/or salts thereof:

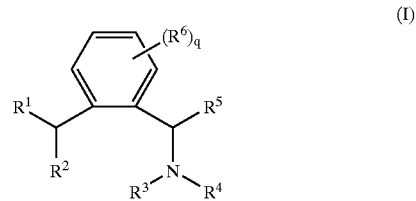

wherein:

$R^1$ is —$C_{1-6}$alkyl;

$R^2$ is -phenyl, unsubstituted, mono- or polysubstituted with a substituent selected from the group consisting of -halo, —$C_{1-6}$alkyl, —$CF_3$, —O—$C_{1-6}$alkyl, and —$NO_2$;

$R^3$ is selected from the group consisting of —H and —$C_{1-6}$alkyl;

$R^4$ is —$C_{1-6}$alkyl;

$R^5$ is —$C_{1-6}$alkyl;

$R^6$ is each independently selected from the group consisting of: -halo, —$C_{1-6}$alkyl, —$CF_3$, —O—$C_{1-6}$alkyl, and —$NO_2$; and q is an integer from 0 to 4.

In certain embodiments, this invention is directed to compounds of the Formula (I) and pharmaceutically acceptable esters, ethers, and/or salts thereof, wherein $R^1$ is —$CH_3$. In one class of these embodiments are those compounds of Formula (I) wherein $R^2$ is -phenyl, unsubstituted, mono- or polysubstituted with a substituent selected from the group consisting of: -halo, —$C_{1-6}$alkyl, —$CF_3$, —O—$C_{1-6}$alkyl, and —$NO_2$, and particularly selected from a group consisting of: -halo, —$C_{1-6}$alkyl, —$CF_3$, and —O—$C_{1-6}$alkyl. In a subclass of these embodiments are those compounds of Formula (I) wherein $R^2$ is selected from the group consisting of: -3-chlorophenyl, -4-chlorophenyl, -4-methoxyphenyl, -3-trifluoromethyl-phenyl, -4-trifluoromethyl-phenyl, -3,4-dichlorophenyl, -3-bromophenyl, -4-bromophenyl and -3-trifluoromethyl-4-chloro-phenyl. In another class of these embodiments are those compounds of Formula (I) wherein $R^3$ is —H; and $R^4$ is —$C_{1-6}$alkyl, and particularly is -methyl. In another class of these embodiments are those compounds of Formula (I) wherein $R^5$ is —$CH_3$. In another class of these embodiments are those compounds of Formula (I) wherein $R^6$ is selected from the group consisting of —$CH_3$ and -halo. In another class of these embodiments are those compounds of Formula (I) wherein q is an integer from 0 to 1 and more particularly q is 0.

Particular novel compounds of structural Formula (I) which may be employed in the methods, uses and compositions of the present invention, include:

(1) Methyl-{1-[2-(1-phenyl-ethyl)-phenyl]-ethyl}-amine
(2) Methyl-{1-[2-(1-phenyl-propyl)-phenyl]-ethyl}-amine
(3) Dimethyl-{1-[2-(1-phenyl-ethyl)-phenyl]-ethyl}-amine
(4) Methyl-{1-[2-(1-phenyl-ethyl)-phenyl]-propyl}-amine (5) (1-{2-[1-(3,4-Dichloro-phenyl)-ethyl]-phenyl}-ethyl)-methyl-amine
(6) {1-[4,5-Dimethyl-2-(1-phenyl-ethyl)-phenyl]-ethyl}-methyl-amine
(7) {1-[4,5-Dichloro-2-(1-phenyl-ethyl)-phenyl]-ethyl}-methyl-amine
(8) (1-{2-[1-(4-Chloro-phenyl)-ethyl]-phenyl}-ethyl)-methyl-amine
(9) (1-{2-[1-(3-Chloro-phenyl)-ethyl]-phenyl}-ethyl)-methyl-amine
(10) (1-{2-[1-(4-Methoxy-phenyl)-ethyl]-phenyl}-ethyl)-methyl-amine
(11) Methyl-(1-{2-[1 (4-trifluoromethyl-phenyl)-ethyl]-phenyl}-ethyl)-amine
(12) Methyl-(1-{2-[1-(3-trifluoromethyl-phenyl)-ethyl]-phenyl})-methyl-amine
(13) (1-{2-[-(3,4-Dichloro-phenyl)-ethyl]-phenyl}-ethyl)-methyl-amine
(14) (1-{2-[1-(4-Bromo-phenyl)-ethyl]-phenyl}-ethyl)-methyl-amine
(15) (1-{2-[1-(3-Bromo-phenyl)-ethyl]-phenyl}-ethyl)-methyl-amine
(16) (1-{2-[1-(4-Bromo-3-trifluoromethyl-phenyl)-ethyl]-phenyl}-ethyl)-methyl-amine and pharmaceutically acceptable salts and tautomers thereof.

Particular novel compounds of structural Formula (I) which may be employed in the methods, uses and compositions of the present invention, include also single enantiomers of the above compounds. For example, methyl-{1-[2-(1-phenyl-ethyl)-phenyl]-ethyl}-amine is meant to include a statistical 1:1:1:1 mixture of [R,R]-methyl-{1-[2-(1-phenyl-ethyl)-phenyl]-ethyl}-amine, [R,S]-methyl-{1-[2-(1-phenyl-ethyl)-phenyl]-ethyl}-amine, [S,R]-methyl-{1-[2-(1-phenyl-ethyl)-phenyl]-ethyl}-amine and [S,S]-methyl-{1-[2-(1-phenyl-ethyl)-phenyl]-ethyl}-amine, and also various other proportions of said enantiomers, wherein one enantiomer is present in a much greater amount than all the other enantiomers, such as e.g. 80:5:5:5, 80:20:0:0, 95:5:0:0, 99:0.5:0.5:0.5:0.5, or when only two of the four enantiomers are present in equal amounts, e.g., 50:50:0:0, 0:0:50:50, or when one enantiomer only is present, e.g., 100:0:0:0, 0:100:0:0, 0:0:100:0, or 0:0:0:100, and many other intermediate combinations.

In other aspects, the invention is directed to pharmaceutical or veterinary compositions of the compounds of formula (I) and pharmaceutically acceptable tautomers and/or salts thereof.

In certain embodiments, this invention is directed to a pharmaceutical composition comprising a pharmaceutically acceptable carrier and as active ingredient the compound of formula (I):

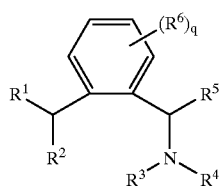

(I)

wherein:
R$^1$ is —C$_{1-6}$alkyl;
R$^2$ is -phenyl, unsubstituted, mono- or polysubstituted with a substituent selected from the group consisting of -halo, —C$_{1-6}$alkyl, —CF$_3$, —O—C$_{1-6}$alkyl, and —NO$_2$;
R$^3$ is selected from the group consisting of —H and —C$_{1-6}$alkyl;

R$_4$ is —C$_{1-6}$alkyl;
R$^5$ is —C$_{1-6}$alkyl;
R$^6$ is each independently selected from the group consisting of: -halo, —C$_{1-6}$alkyl, —CF$_3$, —O—C$_{1-6}$alkyl, and —NO$_2$; and
q is an integer from 0 to 4.

In certain embodiments, this invention is directed a pharmaceutical composition comprising a pharmaceutically acceptable carrier and as active ingredient the compound of Formula I or pharmaceutically acceptable tautomers, and/or salts thereof, wherein R$^1$ is —CH$_3$. In one class of these embodiments are those pharmaceutical compositions comprising a pharmaceutically acceptable carrier and as active ingredient the compound of Formula I or pharmaceutically acceptable esters, ethers, and/or salts thereof wherein R$^2$ is -phenyl, unsubstituted, mono- or polysubstituted with a substituent selected from the group consisting of -halo, —C$_{1-6}$alkyl, —CF$_3$, —O—C$_{1-6}$alkyl, and —NO$_2$, and particularly selected from a group consisting of: -halo, —C$_{1-6}$alkyl, —CF$_3$, and —O—C$_{1-6}$alkyl. In a subclass of these embodiments are those pharmaceutical composition comprising a pharmaceutically acceptable carrier and as active ingredient the compound of Formula I or pharmaceutically acceptable esters, ethers, and/or salts thereof wherein R$^2$ is selected from the group consisting of: -3-chlorophenyl, 4-chlorophenyl, 4-methoxyphenyl, -3-trifluoromethyl-phenyl, -4-trifluoromethyl-phenyl, -3,4-dichlorophenyl, -3-bromophenyl, -4-bromophenyl and -3-trifluoromethyl4-chloro-phenyl. In another class of these embodiments are those pharmaceutical composition comprising a pharmaceutically acceptable carrier and as active ingredient the compound of Formula I or pharmaceutically acceptable esters, ethers, and/or salts thereof wherein R$^3$ is H; and R$^4$ is —C$_{1-6}$alkyl, and particularly is -methyl. In another class of these embodiments are those pharmaceutical composition comprising a pharmaceutically acceptable carrier and as active ingredient the compound of Formula I or pharmaceutically acceptable esters, ethers, and/or salts thereof wherein q is an integer from 0 to 1 and more particularly q is 0.

In other aspects, the invention is directed to methods of treatment of a variety of disorders associated with the serotonergic neural system, such as eating disorders, depression, obsessive compulsive disorders, panic disorders, alcoholism, pain, erectile dysfunction, memory deficits and anxiety; and more particularly depression.

In certain embodiments, this invention is directed to a method of treatment of eating disorders, depression, obsessive compulsive disorders, panic disorders, alcoholism, pain, erectile dysfunction, memory deficits and anxiety, which method comprises administering to a patient in need of such treatment a therapeutically effective amount of the compounds or pharmaceutical compositions disclosed herein.

In other aspects, the invention is directed to methods of treatment of unipolar depression, dysthymia, bipolar depression, treatment-resistant depression, depression in the medically-ill, panic disorder, obsessive-compulsive disorder, eating disorders, social phobia, and premenstrual dysphoric disorder.

In certain embodiments, this invention is directed to a method of treatment of unipolar depression, dysthymia, bipolar depression, treatment-resistant depression, depression in the medically-ill, panic disorder, obsessive-compulsive disorder, eating disorders, social phobia, and premenstrual dysphoric disorder, which method comprises administering to a patient in need of such treatment a therapeutically effective amount of the compounds or pharmaceutical compositions disclosed herein.

"Treatment" includes both therapeutic and prophylactic effects.

DETAILED DESCRIPTION OF THE INVENTION

This invention relates to novel amine compounds, which are potent and selective serotonin reuptake inhibitors. Further, this invention relates to pharmaceutical compositions comprising compounds described herein and to their use as therapeutic agents, particularly in the treatment of neurological disorders.

More specifically, the compounds of this invention are useful in the treatment of a variety of disorders associated with the serotonergic neural system, such as eating disorders, depression, obsessive compulsive disorders, panic disorders, alcoholism, pain, erectile dysfunction, memory deficits, anxiety, unipolar depression, dysthymia, bipolar depression, treatment-resistant depression, depression in the medically-ill, panic disorder, obsessive-compulsive disorder, eating disorders, social phobia, and premenstrual dysphoric disorder. More preferably, the compounds of this invention are useful in the treatment of depressions.

Compounds of formula (I) may be used in combination with other known SSRIs or sequentially with other known SSRIs when a combination formulation is inappropriate. Other SSRIs include, but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., J. Med. Chem., 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761,501. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., Neuropharmacology, 24, 1211–19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofuran carbonitrile, is disclosed in U.S. Pat. No. 4,136,193 as a serotonin reuptake inhibitor. Its pharmacology was disclosed by Christensen et al., Eur. J. Pharmacol., 41, 153 (1977), and reports of its clinical effectiveness in depression may be found in Dufour et al., Int. Clin. Psychopharmacol., 2,225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., Brit. J. Pharmacol., 60, 505 (1977); and De Wilde et al., J. Affective Disord., 4, 249 (1982); and Benfield et al., Drugs, 32, 313 (1986);

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, Eur. J. Pharmacol., 47, 351 (1978); Hassan et al., Brit. J. Clin. Pharmacol., 19, 705 (1985); Laursen et al., Acta Psychiat. Scand., 71, 249 (1985); and Battegay et al., Neuropsychobiology, 13,31 (1985); and Sertraline, (1S-cis)-4-(3,4-dichlorophenyl)-1,2,3,4-tetrahydro-N-methyl-1-naphthylamine hydrochloride, is a serotonin reuptake inhibitor which is marketed as an antidepressant. It is disclosed by U.S. Pat. No. 4,536,518. All of the above-referenced patents are hereby incorporated by reference.

Compounds of formula (I) may be also administered in combination or in succession with other therapeutically effective agents, for example, 5-MCA-NAT (e.g., U.S. Pat. No. 6,562,858), MAO-inhibitors, kappa opioid receptor antagonists (e.g., U.S. Pat. No. 6,528,518), reversible inhibitors of monoamine oxidase (RIMAs), serotonin and noradrenaline reuptake inhibitors (SNRIs), selective neurokinin antagonists (e.g., U.S. Pat. No. 6,436,928) corticotropin releasing factor (CRF) antagonists, antagonists of tachykinins (e.g., U.S. Pat. No. 6,518,273) and α-adrenoreceptor antagonists.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Use of compounds disclosed herein and their analogs in combination with other drugs may reduce the amounts of drugs used in the treatment and thereby alleviating some of the major side effects observed. Furthermore, the period observed between administering the drugs and any observed therapeutic indications may be diminished.

In a further or alternative aspect of the present invention, there is therefore provided a product comprising a compound of formula (I) and an anorectic agent as a combined preparation for simultaneous, separate of sequential use in the treatment or prevention of eating disorders.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamnine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof.

Particularly preferred halogenated amphetamine derivatives of use in combination with a compound of the present invention include: fenfluramine and dexfenfluramine, and pharmaceutically acceptable salts thereof.

Medical Definitions

For convenience, certain terms employed in the specification, examples, and appended claims are collected here.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein, the term "mental disorder" and "mental illness" refer to those provided in the Diagnostic and Statistical Manual (DSM IV), American Psychological Association (APA). These mental disorders include, but are not limited to affective disorders, neurotic disorders and unspecified depressive disorders. Examples of affective disorders include mood disorders, manic disorder, major depressive disorder and bipolar affective disorder. Mood disorders include, but are not limited to, depressive disorders, dysthymic disorder, bipolar disorders (I and II) and cyclothymic disorders. Likewise, examples of neurotic disorders include, but are not limited to, anxiety states, panic disorders, phobias, obsessive-compulsive disorder, post traumatic stress disorder, acute stress disorder, generalized anxiety disorder, attention deficit hyperactivity disorder, Tourette's Syndrome and hysteria Other conditions include sleep disorders, including breathing related sleep disorders.

As used herein, the term "psychosis" means a mental or behavioral disorder, with or without organic damage, causing gross distortion or disorganization of a person's mental capacity, affective response, capacity to recognize reality, communicate, or relate to others such that his or her capacity to cope with the ordinary demands of everyday life is diminished. Psychosis encompasses, but is not limited to, hallucinations, paranoia, affective psychosis (manic psychosis), alcoholic psychoses, arteriosclerotic psychosis, amnestic psychosis, bipolar psychosis (manic- depressive psychosis), Cheyne-Stokes psychosis, climacteric psychosis, depressive psychosis, drug psychosis, dysninesic psychosis, hysterical psychosis, infection-exhaustion psychosis, Korsakoff's psychosis, postinfectious psychosis, postpartum psychosis, posttraumatic psychosis, senile psychosis, situational psychosis, toxic psychosis, traumatic psychosis, Windigo psychosis, schizo-affective psychosis, schizophrenia and related disorders. As used herein, the terms "treatment or prevention of psychosis" and "treating or preventing psychosis" mean the relief from, or prevention of, psychological or physical symptoms of psychosis.

As used herein, the term "schizophrenia" encompasses, but is not limited to, paranoid schizophrenia, disorganized schizophrenia, catatonic schizophrenia and undifferentiated schizophrenia. Positive symptoms of schizophrenia include, but are not limited to: delusions such as delusions of persecution, reference, thought withdrawal and thought insertion; hallucinations such as auditory, visual, olfactory, gustatory and tactile hallucinations; thought disorder; and bizarre behavior. Negative, or deficit, symptoms of schizophrenia include, but are not limited to, blunted affect, poverty of speech, anhedonia and asociality. As used herein, the terms "treatment or prevention of schizophrenia" and "treating or preventing schizophrenia" mean the relief from, or prevention of, positive or negative symptoms of schizophrenia.

As used herein, the meaning of the term "depression" is consistent with its accepted meaning in the art. See, e.g., DSM-IV[R] and *The Merck Manual*, Beers, M. H., et al., eds., 1531–1538 (17 (th )ed. 1999). Psychological symptoms of depression include, but are not limited to, changes in mood, feelings of intense sadness, despair, mental slowing, loss of concentration, pessimistic worry, agitation, and self-deprecation. Physical symptoms of depression include, but are not limited to, insomnia, anorexia, weight loss, decreased energy, and abnormal hormonal circadian rhythms. As used herein, the terms "treatment or prevention of depression" and "treating or preventing depression" mean the relief from, or prevention of, psychological or physical symptoms of depression.

As used herein, the meaning of the term "anxiety" is consistent with its accepted meaning in the art. See, e.g., DSM-IV[R] and *The Merck Manual*, Beers, M. H., et al., eds., 1512–1529 (17 (th )ed. 1999). Anxiety includes, but is not limited to, anxiety attacks, free-floating anxiety, noetic anxiety, separation anxiety, and situation anxiety. Symptoms of anxiety include, but are not limited to, agitation, worry, panic, feelings of fear, helplessness or horror, and obsessive-compulsive behavior. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders. As used herein, the terms "treatment or prevention of anxiety" and "treating or preventing anxiety" mean the relief from, or prevention of, psychological or physical symptoms of anxiety.

As used herein, the term "substance addiction" means the physical and/or psychological addiction to, or dependence on, a substance. Examples of substances to which a patient can be addicted or dependent include, but are not limited to: CNS depressants such as alcohol, barbiturates, ethchlorvynol, glutethimide, methaqualone, methyprylon and natural and synthetic opiate; anxiolytics such as alprazolam, oxazepam, temazepam, chlordiazepoxide and diazepam; stimulants such as amphetamines and methamphetamine in particular, nicotine, and cocaine; and hallucinogens such as LSD, marijuana and mescaline. Psychological symptoms of substance addiction include, but are not limited to, feelings of satisfaction and a desire to repeat the drug experience, craving of the substance, and compulsive use of the substance. Psychological symptoms of substance (i.e., drug or alcohol) withdrawal include, but are not limited to, hallucinations and the symptoms of depression and anxiety disclosed herein. Physical symptoms of substances addiction include, but are not limited to, the physical symptoms of depression defined herein. Physical symptoms of drug withdrawal include pain and the physical symptoms of depression defined herein. As used herein, the terms "treatment or prevention of substance addiction" and "treating or preventing substance addiction" mean the relief from, or prevention of, psychological or physical symptoms of substance addiction or the relief from, or prevention of, psychological or physical symptoms of substance withdrawal.

As used herein, the term "antidepressant compounds" or "antidepressant agents" or simply "antidepressants" includes compounds capable of alleviating the symptoms of depression. Antidepressant compounds are described in, for example, the 1998 SIGMA catalogue and the "The Merck Index", 12th Ed., Budavari et al., eds., Merck & Co., Inc., Rahway, N.J., 1996, the contents of which are incorporated herein by reference.

The term "obsessive-compulsive behavior" and "obsessive-compulsive disorders" refer to actions and/or thoughts which a mammal experiences on a frequent or repetitive basis with little or no volitional control. "Habits" are a very mild, subclinical form of such behavior, but are generally not considered obsessive-compulsive behavior until they become socially debilitating. Subjects exhibiting obsessive-compulsive behaviors are generally aware of their behavior and its abnormality, but are unable to consciously modify their behavior. Examples of obsessive-compulsive behavior include compulsive hand-washing, washing, obsessive counting, continual hand- wringing, and the like.

As used herein, the term "alcoholism" or "physical dependence on alcohol" shall refer to an addictive disease or disorder characterized by an inability to control the intake of alcohol, i.e., a continued excessive or compulsive use of alcoholic drinks. Alcoholism may involve changes in the individual's ability to metabolize alcohol as well. Diagnosis of alcoholism presently can be made by psychiatric examination according to the criteria of DSM-III, axis 1 diagnosis of alcohol dependence, abuse, deterioration, or amnestic disorder (see Hulyalkar et al., 1984, Alcoh. Clin. Exp. Res. 8:337–341).

As used herein, the term "pain" is art recognized and includes a bodily sensation elicited by noxious chemical, mechanical, or thermal stimuli, in a subject, e.g., a mammal such as a human. The term "pain" includes chronic pain, such as lower back pain; pain due to arthritis, e.g., osteoarthritis; joint pain, e.g., knee pain or carpal tunnel syndrome; myofascial pain, and neuropathic pain. The term "pain" further includes acute pain, such as pain associated with muscle strains and sprains; tooth pain; headaches; pain associated with surgery; or pain associated with various forms of tissue injury, e.g., inflammation, infection, and ischemia.

The term "eating disorders" includes anorexia nervosa, bulimia nervosa, and obesity.

The term "serotonergic (SHT) neurons" and "serotonergic neural system" refer to neurons which secrete the neurotransmitter serotonin (5-hydroxytryptamine). SHT neurons typically have a slow, rhythmic pattern of firing and are concentrated in the ventral and ventrolateral aspects of the hindbrain and innervate most parts of the central nervous system including the cerebral cortex, limbic system and spinal cord. 5HT neurons control levels of awareness, arousal, behavior and food intake. The abnormal function of serotonergic neurons has been linked to aggression, depression (including suicidal behavior) and schizophrenia.

The term "therapeutically effective amount" refers to the amount which, when administered to an animal for treating a disease, is sufficient to effect such treatment for the disease.

The term "treating" or "treatment" of a disease in a mammal includes: (1) preventing the disease from occurring in a mammal which may be predisposed to the disease but does not yet experience or display symptoms of the disease, (2) inhibiting the disease, i.e., arresting its development, or (3) relieving symptoms of the disease, i.e., causing regression of the disease.

"Serotonin receptor binding-inhibiting effective," "serotonin reuptake-inhibiting effective" and "therapeutically effective" amounts with respect to the subject method of treatment, refer to an amount of the compounds disclosed herein in a preparation which, when applied as part of a desired dosage regimen are sufficient for inhibiting serotonin reuptake into presynaptic neurons, or serotonin binding to receptors in post-synaptic membranes, in the central nervous systems of mammals, including humans.

A "patient" or "subject" to be treated by the subject method can mean either a human or non-human animal.

Chemical Definitions

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_{1-30}$ for straight chain, $C_{3-30}$ for branched chain), more preferably 20 or fewer, most preferably 6 or fewer. Likewise, preferred cycloalkyls have from 3–10 carbon atoms in their ring structure, and more preferably have 5, 6 or 7 carbons in the ring structure. As used herein "alkyl" is intended to include both branched- and straight-chain saturated aliphatic hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), isopentyl, isohexyl and the like.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g. an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

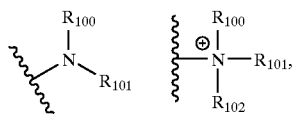

wherein $R_{100}$, $R_{101}$, and $R_{102}$ each independently represent a hydrogen, an alkyl, an alkenyl, —$(CH_2)_m$—$R_{110}$, or $R_{100}$ and $R_{101}$ taken together with the N atom to which they are attached complete a heterocycle having from 4 to 8 atoms in the ring structure; $R_{110}$ represents an aryl, a cycloalkyl, a cycloalkenyl, a heterocycle or a polycycle; and m is zero or an integer in the range of 1 to 8. In preferred embodiments, only one of $R_{100}$ or $R_{101}$ can be a carbonyl, e.g., $R_{100}$, $R_{101}$, and the nitrogen together do not form an imide. In even more preferred embodiments, $R_{100}$ and $R_{101}$, (and optionally $R_{102}$) each independently represent a hydrogen, an alkyl, an alkenyl, or —$(CH_2)_m$—$R_{110}$. Thus, the term "alkylamine" as used herein means an amine group, as defined above, having a substituted or unsubstituted alkyl attached thereto, i.e., at least one of $R_{100}$ and $R_{101}$, is an alkyl group.

The term "acyl amino" is art-recognized and refers to a moiety that can be represented by he general formula:

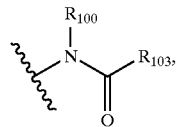

wherein $R_{100}$ as defined above, and $R_{103}$ represents a hydrogen, an alkyl, an alkenyl or —$(CH_2)_m$—$R_{110}$ to, wherein m and $R_{110}$ to are as defined above.

The term "amido" is art recognized as an amino-substituted carbonyl and includes a moiety that can be represented by the general formula:

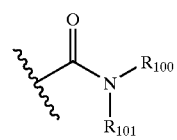

wherein $R_{100}$, $R_{101}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_{110}$, wherein m and R$_{110}$ are defined above. Representative alkylthio groups include methylthio, ethyl thio, and the like.

The term "carbonyl" is art recognized and includes such moieties as can be represented by the general formula:

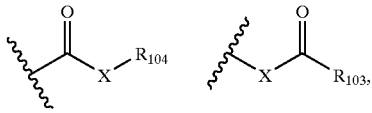

wherein X is a bond or represents an oxygen or a sulfur, and R$_{104}$ represents a hydrogen, an alkyl, an alkenyl, —CH2)$_m$—R$_{110}$ or a pharmaceutically acceptable salt, R$_{103}$ represents a hydrogen, an alkyl, an alkenyl or —(CH$_2$)$_m$—R$_{110}$, where m and R$_{110}$ are as defined above. Where X is an oxygen and R$_{104}$ or R$_{103}$ is not hydrogen, the formula represents an "ester". Where X is an oxygen, and R$_{104}$ is as defined above, the moiety is referred to herein as a carboxyl group, and particularly when R$_{104}$ is a hydrogen, the formula represents a "carboxylic acid". Where X is an oxygen, and R$_{103}$ is a hydrogen, the formula represents a "formate". In general, where the oxygen atom of the above formula is replaced by sulfur, the formula represents a "tiolcarbonyl" group. Where X is a sulfur and R$_{104}$ or R$_{103}$ is not hydrogen, the formula represents a "thiolester." Where X is a sulfur and R$_{104}$ is hydrogen, the formula represents a "thiolcarboxylic acid." Where X is a sulfur and R11' is hydrogen, the formula represents a "Thiolformate." On the other hand, where X is a bond, and R$_{104}$ is not hydrogen, the above formula represents a "ketone" group. Where X is a bond, and R$_{104}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_{110}$, where m and R$_{110}$ are described above.

The term "sulfonate" is art recognized and includes a moiety that can be represented by the general formula:

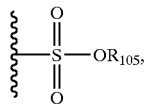

in which R$_{105}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

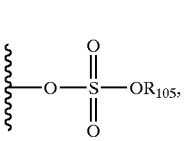

in which R$_{105}$ is as defined above.

The term "sulfonamido" is art recognized and includes a moiety that can be represented by the general formula:

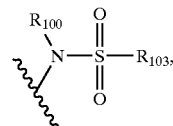

in which R$_{100}$ and R$_{103}$ are as defined above.

The term "sulfamoyl" is art-recognized and includes a moiety that can be represented by the general formula:

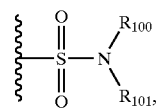

in which R$_{100}$ and R$_{101}$ are as defined above.

The terms "sulfoxido" or "sulfinyl", as used herein, refers to a moiety that can be represented by the general formula:

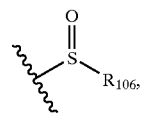

in which R$_{106}$ is selected from the group consisting of hydrogen, alkyl, alkenyl, alkynyl, cycloalkyl, heterocyclyl, aralkyl, or aryl.

A "phosphoryl" can in general be represented by the formula:

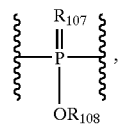

wherein R$_{107}$ represented S or O, and R$_{108}$ represents hydrogen, a lower alkyl or an aryl. When used to substitute, e.g. an alkyl, the phosphoryl group of the phosphorylalkyl can be represented by the general formula:

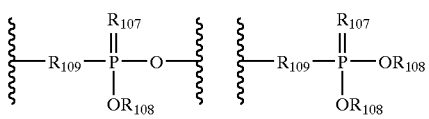

wherein R$_{107}$ represented S or O, and each R$_{108}$ independently represents hydrogen, a lower alkyl or an aryl, R$_{109}$ represents O, S or N. When R$_{107}$ is an S, the phosphoryl moiety is a "phosphorothioate".

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_{110}$, m and R$_{110}$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Under standard nomenclature used throughout this disclosure, the terminal portion of the designated side chain is described first, followed by the adjacent functionality toward the point of attachment. For example, a $C_{1-5}$alkylcarbonylamino-$C_{1-6}$alkyl substituent is equivalent to:

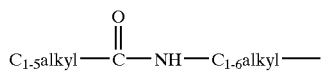

When referring to moieties which may optionally be substituted herein, e.g., alkyl groups, cycloalkyl groups, phenyl groups, heterocycloalkyl groups, and the like, the phrase "unsubstituted, mono- or polysubstituted," as used herein, is intended to mean that the total number of substituents on the moiety overall may be zero, one or more than one, and that each carbon and nitrogen atom available for substitution in the given moiety may independently be unsubstituted or mono- or poly-substituted, with one or more substituents that are the same or different at each occurrence and which result in the creation of a stable structure. The term "polysubstituted" is intended to mean two or more substituents, e.g. di-, tri-, tetra-, penta-substitution and higher as appropriate, valence and stability permitting.

The graphical representation:

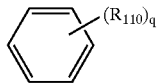

is intended to mean that the phenyl ring is substituted with q $R_{110}$ substituents, i.e., that the number of $R_{110}$ substituents per one phenyl ring is q. The smallest number of $R_{110}$ substituents on a phenyl ring is 0, the highest number is 6. For example, if q=2, there are two $R_{110}$ substituents. The $R_{110}$ substituents may be the same or they may be different depending on the definition of $R_{110}$. The $R_{110}$ substituents may be arranged around the phenyl ring is any number of possible permutations. For example, if q=2 and $R_{110}$= methyl, the above graphical representation would represent o-xylene, m-xylene or p-xylene; if q=2 and $R_{110}$ is selected from the group consisting of -chloro and -methyl, the above graphical representation would represent: o-xylene, m-xylene, p-xylene, 1-chloro-2-methyl-benzene, 1-chloro-3-methyl-benzene, 1-chloro4-methyl-benzene, 1,2-dichloro-benzene, 1,3-dichloro-benzene, or 1,4-dichloro-benzene. When q=0, no $R_{110}$ groups are attached to the phenyl ring unless any such groups are explicitly drawn into the structure.

Where there are no $R_{110}$ substituents, all substituents on the phenyl ring are —H, unless any other substituents are explicitly drawn into the structure.

The graphical representation:

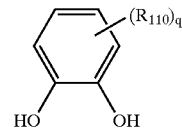

is intended to mean that the catechol is substituted with q $R_{110}$ substituents, i.e., that the number of $R_{110}$ substituents per one catechol is q. For example, if q=2 and $R_{110}$=methyl, the above graphical representation would represent 3,4-dimethyl-benzene-1,2-diol, 3,5-dimethyl-benzene-1,2-diol, 3,6-dimethyl-benzene-1,2-diol, 4,5-dimethyl-benzene-1,2-diol; if q=2 and $R_{110}$ is selected from the group consisting of -chloro and -methyl, the above graphical representation would represent: 3,4dimethyl-benzene-1,2-diol, 3,5-dimethyl-benzene-1,2-diol, 3,6-dimethyl-benzene-1,2-diol, 4,5-dimethyl-benzene-1,2-diol, 3,4-dichloro-benzene-1,2-diol, 3,5-dichloro-benzene-1,2-diol, 3,6-dichloro-benzene-1,2-diol, 4,5-dichloro-benzene-1,2-diol, 3-chloro-4-methyl-benzene-1,2-diol, 3-chloro-5-methyl-benzene-1,2-diol, 3-chloro-6-methyl-benzene-1,2-diol, 4-chloro-3-methyl-benzene-1,2-diol, 4-chloro-5-methyl-benzene-1,2-diol, or 5-chloro-3-methyl-benzene-1,2-diol.

Certain compounds of the present invention may exist in particular geometric or stereoisomeric forms. "Stereoisomers" are compounds that have the same sequence of covalent bonds and differ in the relative disposition of their atoms in space. Stereoisomers fall within two broad classes: optical isomers and geometric isomers. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "tautomers," as used herein, refers to isomers that are readily interconvertible through rapid equilibration. For example, certain tautomers may undergo rapid proton shifts from one atom of the compound to another atom of the compound. Such an example may be a ketone and its enol form known as keto-enol tautomers. Some of the compounds described herein may exist as tautomers, including but not limited to keto-enol tautomers. The individual tautomers of the compounds of Formula I, as well as mixtures thereof, are included in the scope of this invention.

Contemplated equivalents of the compounds described above include compounds which otherwise correspond thereto, and which have the same general properties thereof (e.g. the ability to selectively inhibit serotonin reuptake), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "amino acid," comprises the residues of the natural amino acids (e.g. Ala, Arg, Asn, Asp, Cys, Glu, Gln, Gly, His, Hyl, Hyp, lle, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C1–C6)alkyl, phenyl or benzyl ester or amide; or as an a-methylbenzyl amide). Other suitable amino and carboxy protecting groups are known to those skilled in the art (See for example, T. W. Greene, Protecting Groups In Organic Synthesis; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2nd ed.; Wiley: New York, 1991).

The term "prodrug" is intended to encompass compounds which, under physiological conditions, are converted into the therapeutically active agents of the present invention. A common method for making a prodrug is to select moieties which are hydrolyzed under physiological conditions to provide the desired. In other embodiments, the prodrug is converted by an enzymatic activity of the host animal.

A list of many of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

Pharmaceutical Compositions

While it is possible for a compound of the present invention to be administered alone, it is preferable to administer the compound as a pharmaceutical formulation (composition). The compounds according to the invention may be formulated for administration in any convenient way for use in human or veterinary medicine.

Thus, another aspect of the present invention provides pharmaceutically acceptable compositions comprising a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "therapeutically-effective amount" as used herein means that amount of a compound, material, or composition comprising a compound of the present invention which is effective for producing some desired therapeutic effect by inhibiting reuptake of serotonin, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present antitumor agents may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamnine, ethanolamine, diethanolamine, piperazine and the like. (See, for example, Berge et al. supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediarnine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient.

A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or salicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, beta- and $\gamma$-cyclodextrin, dimethyl $\beta$-cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compounds of the present invention.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal; and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compounds of the present invention in the proper medium. Absorption enhancers can also be used to increase the flux of the compounds of the present invention across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained; for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition". W.H. Freedman and CO., San Francisco, U.S.A., 1969 or "Livestock Feeds and Feeding" O and B books. Corvallis, Oreg., U.S.A., 1977).

Administration

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular apoptosis-inducing agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutical effects of the first administered one is not entirely disappeared when the subsequent is administered.

Synthetic Schemes

Compounds of the present invention may be prepared by standard organic manipulations well-known to those skilled in the art. Specifically, the synthesis of compounds of formula I can be accomplished using the approach outlined below:

(−)-alpha-methylbenzylamine, (+)- or (−)-alpha-1-naphthyl) ethylamine, and the like. Examples of suitable solvents include ethanol, isopropyl alcohol, benzene, acetonitrile, nitromethane, acetone, and the like. Two diasteromeric salts form in the solution, one salt usually being less soluble than the other. Repetitive recrystallization of the crystalline salt generally affords a pure diastereomeric salt from which is obtained the desired pure enantiomer, for example, by acidification of the salt with a mineral acid, filtration, and recrystallization.

The other optically pure antipode may generally be obtained by using a different optically active base to form the diastereomeric salt. It may be advantageous to isolate the partially resolved acid from the filtrates of the purification of the first diasteromeric salt, described above, and to purify further this substance through the use of another optically active base. It is especially advantageous for isolating the second enantiomer to use an optically active base that is the antipode of the base used for isolating the first enantiomer. For example, if (+)-alpha-methylbenzylamine was used first, then (−)-alpha methylbenzylamine would be used to isolate the second (remaining) enantiomer.

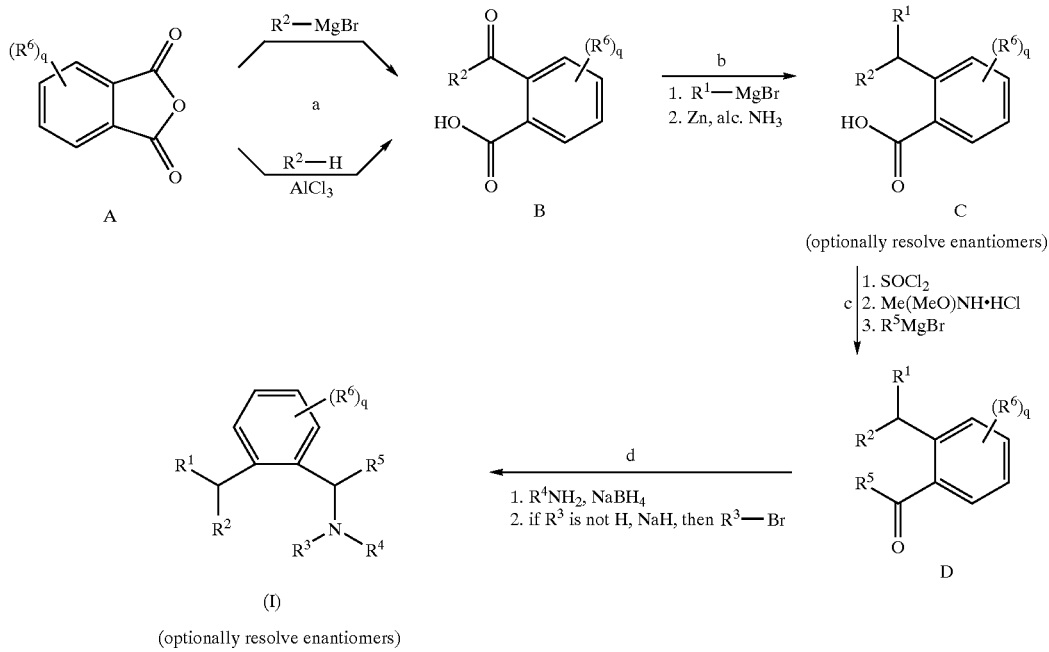

In step a, benzoylbenzoic acids (B) are prepared from commercially available phthalic anhydrides (A) by reaction with an appropriate Grignard reagent or via a Friedel-Crafts reaction with appropriately substituted or unsubstituted benzene. (See, e.g., Topliss, et al., 1964, Journal of Medicinal Chemistry, 7(4), 453; U.S. Pat. No. 4,500,636; Aeberli, et al., 1975, Journal of Medicinal Chemistry, 18(2), 177).

In step b, benzoylbenzoic acids (B) are converted to benzoic acid intermediates (C) by reaction with an appropriate Grignard reagents (to give a phthalide), followed by reduction of the resultant phthalide with zinc and alcoholic ammonia (See, e.g., Heymann et al., 1950, JACS, 72, 84–6; Bergman, 1939, JOC, 4, 1). At this stage benzoic acid intermediates (C) may be resolved into their pure enantiomers, or into mixtures enriched in one of the two enantiomers, by one or more methods known in the art. For example, intermediates C may be resolved by forming in a suitable solvent a salt of the racemic mixture with an optically active base such as (+)- or (−)amphetamine, brucine, (+)- cinchonine, (−) cinchonidine, strychine, (+)- or In step c, benzoic acid intermediates C are converted to ketones D by converting them to acid chlorides with thionyl chloride first, followed by reaction with N,O-dimethylhydroxylamine hydrochloride to form the corresponding Weinreb amides (see, e.g., Weinreb et al., 1985, Tetrahedron Lett., 22(39), 3815; De Luca et al., 2001, JOC, 66, 2534), and followed by a reaction with an appropriate Grignard reagent.

In the final step, step d, ketones D are converted to compounds of Formula (I) by reductive amination with primary amines and sodium borohydride or sodium cyanoborohydride, followed when appropriate (i.e., when $R^3 \neq H$) by a reaction with a suitable base and an alkyl bromide.

At this final stage, compounds of Formula I may be resolved into their pure enantiomers, or into mixtures enriched in one of the two enantiomers, by one or more methods known in the art. For example, compounds of Formula I may be resolved by forming in a suitable solvent a salt of the racemic mixture with an optically active acid, such as (−)-di-p-toluoyl-d-tartaric acid or (+)-di-p-toluoyl-l-tartaric acid. Examples of suitable solvents include ethanol, isopropyl alcohol, benzene, acetonitrile, nitromethane, acetone, and the like. Two diasteromeric salts form in the solution, one salt usually being less soluble than the other. Repetitive recrystallization of the crystalline salt generally affords a pure or enriched diastereomeric salt from which is obtained the desired pure enantiomer or enriched mixture of enantiomers, for example, by acidification of the salt with a mineral acid, filtration, and recrystallization.

The other optically pure antipode may generally be obtained by using a different optically active acid to form the diastereomeric salt. It may be advantageous to isolate the partially resolved acid from the filtrates of the purification of the first diastereomeric salt, described above, and to purify further this substance through the use of another optically active base. It is especially advantageous for isolating the second enantiomer to use an optically active acid that is the antipode of the acid used for isolating the first enantiomer. For example, if (−)-di-p-toluoyl-d-tartaric acid was used first, then(+)di-p-toluoyl-l-tartaric acid would be used to isolate the second (remaining) enantiomer.

All literature articles, books, and patents referenced herein are incorporated herein in their entirety.

EXAMPLES

Example 1

Methyl-{1-[2-(1-phenyl-ethyl)-phenyl]-ethyl}-amine.

The identity of methyl-{1-[2-(1-phenyl-ethyl)-phenyl]-ethyl}-amine was confirmed by NMR, elemental analysis and mass spectrometry. EI-MS m/z 240 [M+H]$^+$ confirmed the molecular formula to be $C_{17}H_{21}N$. Anal. Calcd. for $C_{17}H_{21}N$: C, 85.3; H, 8.84; N, 5.85. Found C, 85.4; H, 8.88; N, 5.72

Example 2

Methyl-{1-[2-(1-phenyl-propyl)-phenyl]-ethyl}-amine.

The identity of methyl-{1-[2-(1-phenyl-propyl)-phenyl]-ethyl}-amine was confirmed by NMR, elemental analysis and mass spectrometry. EI-MS m/z 254 [M+H]$^+$ confirmed the molecular formula to be $C_{18}H_{23}N$. Anal. Calcd. for $C_{18}H_{23}N$: C, 85.3; H, 9.15; N, 5.53. Found C, 85.3; H, 9.12; N, 5.58.

Example 3

Dimethyl-{1-[2-(1-phenyl-ethyl)-phenyl]-ethyl}-amine.

The identity of dimethyl-{1-[2-(1-phenyl-ethyl)-phenyl]-ethyl}-amine was confirmed by NMR, elemental analysis and mass spectrometry. EI-MS m/z 254 [M+H]$^+$ confirmed the molecular formula to be $C_{18}H23N$. Anal. Calcd. for $C_{18}H_{23}N$: C, 85.3; H, 9.15; N, 5.53. Found C, 85.3; H, 9.14; N, 5.60.

Example 4

Methyl-{1-[2-(1-phenyl-ethyl)-phenyl]-propyl}-amine

The identity of methyl-{1-[2-(1-phenyl-ethyl)-phenyl]-propyl}-amine was confirmed by NMR, elemental analysis and mass spectrometry. EI-MS m/z 254 [M+H]$^+$ confirmed the molecular formula to be $C_{18}H_{23}N$. Anal. Calcd. for $C_{18}H_{23}N$: C, 85.3; H, 9.15; N, 5.53. Found C, 85.4; H, 9.11; N, 5.53.

Example 5

(1-{2-[1-(3,4-Dichloro-phenyl)ethyl]-phenyl}-ethyl)-methyl-amine

The identity of (1-{2-[1-(3,4-Dichloro-phenyl)-ethyl]-phenyl}-ethyl)-methyl-amine was confirmed by NMR, elemental analysis and mass spectrometry. EI-MS m/z 308 [M+H]$^+$ confirmed the molecular formula to be $C_{17}H_{19}Cl_2N$. Anal. Calcd. for $C_{17}H_{19}Cl_2N$: C, 66.2; H, 6.21; N, 4.54. Found C, 66.1; H, 6.24; N, 4.58.

Example 6

{1-[4,5-Dimethyl-2-(1-phenyl-ethyl)-phenyl]-ethyl}-methyl-amine

The identity of {1-[4,5-Dimethyl-2-(1-phenyl-ethyl)-phenyl]-ethyl}-methyl-amine was confirmed by NMR, elemental analysis and mass spectrometry. EI-MS m/z 268 [M+H]$^+$ confirmed the molecular formula to be $C_{19}H_{25}N$. Anal. Calcd. for $C_{19}H_{25}N$: C, 85.3; H, 9.42; N, 5.24. Found C, 85.3; H, 9.39; N, 5.30.

Example 7

{1-[4,5-Dichloro-2-(1-phenyl-ethyl)-phenyl]-ethyl}-methyl-amine.

The identity of {1-[4,5-Dichloro-2-(1-phenyl-ethyl)-phenyl]-ethyl}-methyl-amine was confirmed by NMR, elemental analysis and mass spectrometry. EI-MS m/z 308 [M+H]$^+$ confirmed the molecular formula to be $C_{17}H_{19}Cl_2N$. Anal. Calcd. for $C_{17}H_{19}Cl_2N$: C, 66.2; H, 6.21; N, 4.54. Found C, 66.2; H, 6.17; N, 4.60.

Example 8

(1-{2-[1-(4-Chloro-phenyl)-ethyl]-phenyl}-ethyl)-methyl-amine.

The identity of (1-{2-[1-(4-Chloro-phenyl)-ethyl]-phenyl}-ethyl)-methyl-amine was confirmed by NMR, elemental analysis and mass spectrometry. EI-MS m/z 274 [M+H]$^+$ confirmed the molecular formula to be $C_{17}H_{20}ClN$. Anal. Calcd. for $C_{17}H_{20}ClN$: C, 74.6; H, 7.36; N, 5.12. Found C, 74.6; H, 7.38; N, 5.17.

Example 9

(1-{2-[1-(3-Chloro-phenyl)-ethyl]-phenyl}-ethyl)-methyl-amine.

The identity of (1-{2-[1-(3-Chloro-phenyl)-ethyl]-phenyl}-ethyl)-methyl-amine was confirmed by NMR, elemental analysis and mass spectrometry. EI-MS m/z 274 [M+H]$^+$ confirmed the molecular formula to be $C_{17}H_{20}ClN$. Anal. Calcd. for $C_{17}H_{20}ClN$: C, 74.6; H, 7.36; N, 5.12. Found C, 74.7; H, 7.32; N, 5.15.

Example 10

(1-{2-[1-(4-Methoxy-phenyl)-ethyl]-phenyl}-ethyl)-methyl-amine.

The identity of (1-{2-[1-(4-Methoxy-phenyl)-ethyl]-phenyl}-ethyl)-methyl-amine was confirmed by NMR, elemental analysis and mass spectrometry. EI-MS m/z 270 [M+H]$^+$ confirmed the molecular formula to be $C_{18}H_{23}NO$. Anal. Calcd. for $C_{18}H_{23}NO$: C, 80.3; H, 8.61; N, 5.20. Found C, 80.3; H, 8.64; N, 5.16.

Example 11

Methyl-(1-{2-[1-(4-trifluoromethyl-phenyl)-ethyl]-phenyl}-ethyl)-amine.

The identity of methyl-(1-{2-[1-(4-trifluoromethyl-phenyl)-ethyl]-phenyl}-ethyl)-amine was confirmed by NMR, elemental analysis and mass spectrometry. EI-MS m/z 308 [M+H]$^+$ confirmed the molecular formula to be $C_{18}H_{20}F_3N$. Anal. Calcd. for $C_{18}H_{20}F_3N$: C, 70.3; H, 6.56; N, 4.56. Found C, 70.3; H, 6.58; N, 4.60.

Example 12

Methyl-(1-{2-[1-(3-triluoromethyl-phenyl)-ethyl]-phenyl}-ethyl)-amine.

The identity of methyl-(1-{2-[1-(3-trifluoromethyl-phenyl)-ethyl]-phenyl}-ethyl)-amine was confirmed by NMR, elemental analysis and mass spectrometry. EI-MS m/z 308 [M+H]$^+$ confirmed the molecular formula to be $C_{18}H_{20}F_3N$. Anal. Calcd. for $C_{18}H_{20}F_3N$: C, 70.3; H, 6.56; N, 4.56. Found C, 70.2; H, 6.56; N, 4.58.

Example 13

(1-{2-[1-(3,4-Dichloro-phenyl)-ethyl]-phenyl}-ethyl)-methyl-amine.

The identity of (1-{2-[1-(3,4-Dichloro-phenyl)ethyl]-phenyl}-ethyl)-methyl-amine was confirmed by NMR, elemental analysis and mass spectrometry. EI-MS m/z 308 [M+H]$^+$ confirmed the molecular formula to be $C_{17}H_{19}Cl_2N$. Anal. Calcd. for $C_{17}H_{19}Cl_2N$: C, 66.2; H, 6.21; N, 4.54. Found C, 66.2; H, 6.24; N, 4.58.

Example 14

(1-{2-[1-(4-Bromo-phenyl)ethyl]-phenyl}-ethyl)-methyl-amine.

The identity of (1-{2-[1-(4-Bromo-phenyl)-ethyl]-phenyl}-ethyl)-methyl-amine was confirmed by NMR, elemental analysis and mass spectrometry. EI-MS m/z 318 [M+H]$^+$ confirmed the molecular formula to be $C_{17}H_{20}BrN$. Anal. Calcd. for $C_{17}H_{20}BrN$: C, 64.2; H, 6.33; N, 4.40. Found C, 64.1; H, 6.35; N, 4.45.

Example 15

Methyl-(1-{2-[1-(4-trifluoromethyl-phenyl)-ethyl]-phenyl}-ethyl)-amine.

The identity of methyl-(1-{2-[1-(4-trifluoromethyl-phenyl)ethyl]-phenyl}-ethyl-amine was confirmed by NMR, elemental analysis and mass spectrometry. EI-MS m/z 308 [M+H]$^+$ confirmed the molecular formula to be $C_{18}H_{20}F_3N$. Anal. Calcd. for $C_{18}H_{20}F_3N$: C, 70.3; H, 6.56; N, 4.56. Found C, 70.3; H, 6.58; N, 4.60.

Example 16

(1-{2-[1-(3-Bromo-phenyl)-ethyl]-phenyl}-ethyl)-methyl-amine.

The identity of (1-{2-[1-(3-Bromo-phenyl)-ethyl]-phenyl}-ethyl)-methyl-amine was confirmed by NMR, elemental analysis and mass spectrometry. EI-MS m/z 318 [M+H]$^+$ confirmed the molecular formula to be $C_{17}H_{20}BrN$. Anal. Calcd. for $C_{17}H_{20}BrN$: C, 64.2; H, 6.33; N, 4.40. Found C, 64.2; H, 6.36; N, 4.43.

Example 17

(1-{2-[1-(4-Bromo-3-trifluoromethyl-phenyl)-ethyl]-phenyl}-ethyl)-methyl-amine.

The identity of (1-{2-[1-(4-Bromo-3-trifluoromethyl-phenyl)-ethyl]-phenyl}-ethyl)-methyl-amine was confirmed by NMR, elemental analysis and mass spectrometry. EI-MS m/z 386 [M+H]$^+$ confirmed the molecular formula to be $C_{18}H_{19}BrF_3N$. Anal. Calcd. for $C_{18}H_{19}BrF_3N$: C, 56.0; H, 4.96; N, 3.63. Found C, 56.2; H, 4.92; N, 3.65.

Example 18

Ability of (1-{2-[1-(3,4-Dichloro-phenyl)-ethyl]-phenyl}-ethyl)-methyl-amine Hydrochloride to Antagonize Parachloroamphetamine (PCA)-induced Depletion of Serotonin Levels from Rat Brain In Vivo Serotonin uptake blockers show a dose-dependent antagonism of the serotonin-depleting action of PCA, a drug which requires 5HT uptake into 5HT neurons to exert its effect. Sprague-Dawley CD male rats (180–230 g.) in groups of five received two simultaneous subcutaneous injections: either the named test compound (at different dosage levels)+ 6.6 mg/kg body weight PCA, water+6.6 mg/kg body weight PCA, or water+water (controls). The rats were decapitated four hours later and their whole brain assayed for serotonin content by the Bogdanski method. Homogenates of brain in 0.1N HCl were made alkaline with borate buffer and extracted with butanol. The solvent phase was then extracted with 0.1N HCl. The aqueous extracts were acidified with concentrated HCl and the intrinsic fluorescence of serotonin measured in a spectrophotofluorometer. The $ED_{50}$, i.e., the dose giving a 50% reversal of the PCA-induced serotonin depletion, was estimated to be 0.1 mg/kg body weight. Similarly, the $ED_{50}$ for other compounds in Examples 1–17 were determined and were <0.3 mg/kg.

Example 19

Reduction of Behavioral Despair In Vivo (Modified Porsolt Method) by (1-{2-[1-(3,4-Dichloro-phenyl)-ethyl]-phenyl}-ethyl)-methyl-amine hydrochloride.

A modification of the procedure described by Porsolt et al., Arch. Int. Pharmnacodyn., 229, pp. 327–336 (1977) was used. A number of Swiss-Webster CD male mice weighing 25–30 g. were housed under standard laboratory conditions for at least one week prior to experimentation. Groups of 10 mice were then injected subcutaneously with either a given dosage of the named test compound or vehicle (5% Emulphor: 5% ethanol: 90% normal saline). One hour later the mice were placed individually in 1 liter beakers containing 7 cm of 25° C. water. Beginning at 2 min. after immersion, each mouse was observed every 30 sec. for the presence of immobility, characterized as floating motionless in the water. A total of ten observations were made, each being scored as "0=animal moving, swimming, attempting to escape" or "1=animal immobile". The number of positive observations for each mouse was then totaled and a mean immobility score calculated for the group of ten. For dose-response analysis, this data was converted to % MPE (maximum possible effect) values, defined as: (Control mean—Test Mean)/Control Mean×100%. From the % MPE data a % $MPE_{50}$ value, i.e. the dosage producing a 50% reduction in immobility relative to control, was determined by linear regression analysis to be 5.2 mg/kg body weight for the named test compound. Similarly, the % $MPE_{50}$ values were determined for other compounds in examples 1–17 and were <8.0 mg/kg.

I claim:

1. The compound of formula I and the pharmaceutically acceptable salts and tautomers thereof:

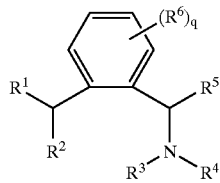

wherein:

R$^1$ is —C$_{1-6}$alkyl;

R$^2$ is -phenyl, unsubstituted, mono- or polysubstituted with a substituent selected from the group consisting of -halo, —C$_{1-6}$alkyl, —CF$_3$, —O—C$_{1-6}$alkyl, and —NO$_2$;

R$^3$ is selected from the group consisting of —H and —C$_{1-6}$alkyl;

R$^4$ is —C$_{1-6}$alkyl;

R$^5$ is —C$_{1-6}$alkyl;

R$^6$ is each independently selected from the group consisting of: -halo, —C$_{1-6}$alkyl, —CF$_3$, —O—C$_{1-6}$alkyl, and —NO$_2$; and q is an integer from 0 to 4.

2. The compound of claim 1 and the pharmaceutically acceptable salts and tautomers thereof, wherein R$^1$ is -methyl.

3. The compound of claim 2 and the pharmaceutically acceptable salts and tautomers thereof, wherein R$^2$ is -phenyl, unsubstituted, mono- or polysubstituted with a substituent selected from the group consisting of: -halo, —C$_{1-6}$alkyl, —CF$_3$, and —O—C$_{1-6}$alkyl.

4. The compound of claim 3 and the pharmaceutically acceptable salts and tautomers thereof, wherein R$^2$ is selected from the group consisting of: -3-chlorophenyl, 4-chlorophenyl, -4-methoxyphenyl, -3-trifluoromethyl-phenyl, -4-trifluoromethyl-phenyl, -3,4-dichlorophenyl, -3-bromophenyl, -4-bromophenyl and -3-trifluoromethyl-4-chloro-phenyl.

5. The compound of claim 3 and the pharmaceutically acceptable salts and tautomers thereof, wherein R$^3$ is —H.

6. The compound of claim 4 and the pharmaceutically acceptable salts and tautomers thereof, wherein R$^3$ is —H.

7. The compound of claim 5 and the pharmaceutically acceptable salts and tautomers thereof, wherein R$^4$ is —CH$_3$.

8. The compound of claim 6 and the pharmaceutically acceptable salts and tautomers thereof, wherein R$^4$ is —CH$_3$.

9. The compound of claim 7 and the pharmaceutically acceptable salts and tautomers thereof, wherein R$^5$ is —CH$_3$.

10. The compound of claim 8 and the pharmaceutically acceptable salts and tautomers thereof, wherein R$^5$ is —CH$_3$.

11. The compound of claim 9 and the pharmaceutically acceptable salts and tautomers thereof, wherein R$^6$ is selected from the group consisting of —CH$_3$ and -halo.

12. The compound of claim 10 and the pharmaceutically acceptable salts and tautomers thereof, wherein R$^6$ is selected from the group consisting of —CH$_3$ and -halo.

13. The compound of claim 11 and the pharmaceutically acceptable salts and tautomers thereof, wherein q is 0 to 2.

14. The compound of claim 12 and the pharmaceutically acceptable salts and tautomers thereof, wherein q is 0 to 2.

15. The compound of claim 1, wherein said compound is selected from the group consisting of:

(1) Methyl-{1-[2-(1-phenyl-ethyl)-phenyl]-ethyl}-amine, (2) Methyl-{1-[2-(1-phenyl-propyl)-phenyl]-ethyl}-amine, (3) Dimethyl-{1-[2-(1-phenyl-ethyl)-phenyl]-ethyl}-amine, (4) Methyl-{1-[2-(1-phenyl-ethyl)-phenyl]-propyl}-amine, (5) (1-{2-[1-(3,4-Dichloro-phenyl)-ethyl]-phenyl}-ethyl)-methyl-amine, (6) {1-[4,5-Dimethyl-2-(1-phenyl-ethyl)-phenyl]-ethyl}-methyl-amine, (7) {1-[4,5-Dichloro-2-(1-phenyl-ethyl)-phenyl]-ethyl}-methyl-amine, (8) (1-{2-[1-(4-Chloro-phenyl)-ethyl]-phenyl}-ethyl)-methyl-amine, (9) (1-{2-[1-(3-Chloro-phenyl)-ethyl]-phenyl}-ethyl)-methyl-amine,

(10) (1-{2-[1-(4-Methoxy-phenyl)-ethyl]-phenyl}-ethyl)-methyl-amine,

(11) Methyl-(1-{2-[1-(4-trifluoromethyl-phenyl)-ethyl]-phenyl}-ethyl)-amine,

(12) Methyl-(1-{2-[1-(3-trifluoromethyl-phenyl)-ethyl]-phenyl}-ethyl)-amine,

(13) (1-{2-[1-(3,4-Dichloro-phenyl)-ethyl]-phenyl}-ethyl)-methyl-amine,

(14) (1-{2-[1-(4-Bromo-phenyl)-ethyl]-phenyl}-ethyl)-methyl-amine,

(15) (1-{2-[1-(3-Bromo-phenyl)-ethyl]-phenyl}-ethyl)-methyl-amine, and

(16) (1-{2-[1-(4-Bromo-3-trifluoromethyl-phenyl)-ethyl]-phenyl}-ethyl)-methyl amine, and pharmaceutically acceptable salts and tautomers thereof.

16. A pharmaceutical composition comprising a pharmaceutically acceptable carrier and as active ingredient the compound of formula I and pharmaceutically acceptable salts and tautomers thereof:

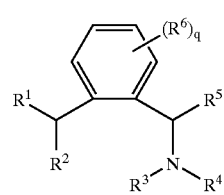

wherein:

R$^1$ is —C$_{1-6}$alkyl;

R$^2$ is -phenyl, unsubstituted, mono- or polysubstituted with a substituent selected from the group consisting of -halo, —C$_{1-6}$alkyl, —CF$_3$, —O—C$_{1-6}$alkyl, and —NO$_2$;

R³ is selected from the group consisting of —H and —C$_{1-6}$alkyl;

R⁴ is —C$_{1-6}$alkyl;

R⁵ is —C$_{1-6}$alkyl;

R⁶ is each independently selected from the group consisting of: -halo, —C$_{1-6}$alkyl, —CF$_3$, —O—C$_{1-6}$alkyl, and —NO$_2$; and q is an integer from 0 to 4.

17. A method of treating depression in a patent, which method comprises administering to a patient a therapeutically effective amount of the compound of claim 1.

18. The method of claim 17, wherein said depression is selected from the group consisting of: unipolar depression, dysthymia, bipolar depression, treatment-resistant depression, and depression in the medically-ill.

* * * * *